United States Patent [19]
Goux et al.

[11] Patent Number: 5,567,320
[45] Date of Patent: Oct. 22, 1996

[54] METHOD FOR THE DETERMINATION OF A SIGNIFICANT PARAMETER OF THE PROGESS OF AN EXTRACORPOREAL TREATMENT OF BLOOD

[75] Inventors: Nicolas Goux, Craponne; Bernard Bene, Irigny, both of France

[73] Assignee: Hospal AG, Basel, Switzerland

[21] Appl. No.: 358,175

[22] Filed: Dec. 16, 1994

[30] Foreign Application Priority Data

Dec. 17, 1993 [FR] France .................................. 93 15527
Mar. 23, 1994 [FR] France .................................. 94 03710

[51] Int. Cl.⁶ .......................... B01D 61/32; A61M 37/00
[52] U.S. Cl. .......................... 210/739; 128/692; 210/96.2; 210/645; 210/646; 604/4
[58] Field of Search ..................... 210/96.1, 96.2, 210/645, 646, 647, 739, 929; 364/413.01, 413.02, 413.03, 413.07, 413.11; 604/4–6, 29; 128/691, 692

[56] References Cited

U.S. PATENT DOCUMENTS

| | | | |
|---|---|---|---|
| 4,508,622 | 4/1985 | Polaschegg et al. | 210/96.2 |
| 4,668,400 | 5/1987 | Veech | 210/647 |
| 4,923,613 | 5/1990 | Chevallet | 210/647 |
| 5,100,554 | 3/1992 | Polaschegg | 210/647 |
| 5,230,702 | 7/1993 | Lindsay et al. | 604/4 |
| 5,399,157 | 3/1995 | Goux et al. | 604/5 |
| 5,403,497 | 4/1995 | Schultz | 210/96.1 |

FOREIGN PATENT DOCUMENTS

| | | |
|---|---|---|
| 0291421 | 11/1988 | European Pat. Off. . |
| 428927 | 11/1989 | European Pat. Off. . |
| 547025 | 6/1993 | European Pat. Off. . |

*Primary Examiner*—Joseph W. Drodge
*Attorney, Agent, or Firm*—Finnegan, Henderson, Farabow, Garrett & Dunner, L.L.P.

[57] ABSTRACT

A method for determining a significant parameter (Cb, D, K, Kt/V) of the progress of an extracorporeal blood treatment carried-out using a membrane exchanger, includes the steps of successively circulating three treatment fluids through the exchanger. Each fluid has a characteristic Cd linked to at least one of the significant parameters of the treatment (Cb, D, K, Kt/V). The value of the characteristic in the first fluid upstream of the exchanger is different from the value of the characteristic in the second fluid upstream of the exchanger, the latter being itself different from the value of the characteristic in the third fluid upstream of the exchanger. Two values for each of the three treatment fluids are measured, respectively upstream and downstream of the exchanger, and at least one value of at least one significant parameter of the progress of the treatment (Cb, D, K, Kt/V) is calculated from the measured values.

18 Claims, 1 Drawing Sheet

5,567,320

METHOD FOR THE DETERMINATION OF A SIGNIFICANT PARAMETER OF THE PROGRESS OF AN EXTRACORPOREAL TREATMENT OF BLOOD

BACKGROUND OF THE INVENTION

1. Field of the Invention

The invention relates to a method for the determination of a significant parameter of the progress of an extracorporeal treatment of blood, in particular of a purification treatment intended to palliate renal insufficiency, such as haemodialysis or haemodiafiltration.

2. Description of the Related Art

Haemodialysis consists of circulating, on both sides of the semipermeable membrane of an exchanger, the blood of a patient or a treatment fluid which is substantially isotonic to blood, so that, during the diffusive transfer which is established across the membrane for the substances having different concentrations on either side of the membrane, the blood impurities (urea, creatinine and the like) migrate from the blood towards the treatment fluid. The electrolytic concentration of the treatment fluid is also generally chosen in order to correct the electrolytic concentration of the patient's blood.

In a haemodiafiltration treatment, to the diffusive transfer obtained by dialysis is added a convective transfer by ultrafiltration resulting from a positive pressure difference created between the blood side and the treatment fluid side of the membrane.

It is of greatest interest to be able to determine, throughout a treatment session, one or more significant parameters of the progress of the treatment in order to be able, where appropriate, to modify the treatment conditions as initially set for the purpose of a determined therapeutic objective.

The parameters of which knowledge makes it possible to monitor the progress of the treatment, that is to say also to evaluate the correspondence between the treatment conditions initially set and the therapeutic objective, are in particular the blood concentration of a given solute (for example sodium), the real dialysance or the real clearance of the exchanger for such solute (the dialysance and the clearance representing the purification efficiency of the exchanger), or the dose of dialysis administered after a treatment time t, which, according to the work of Sargent and Gotch, can be assimilated to the dimensionless ratio $Kt/V$, where $K$ is the real clearance for urea, $t$ the treatment time elapsed, and $V$ the volume of distribution of urea, that is to say the total volume of water of the patient (Gotch FA, Sargent SA. A mechanistic analysis of the National Cooperative Dialysis Study (NCDS). Kidney int 1985; 28: 526–34).

All these parameters pose the same problem for their determination, which is to necessitate the precise knowledge of a physical or chemical characteristic of the blood, whereas this characteristic cannot, in practice, be obtained by direct measurement on a sample for therapeutic, prophylactic and financial reasons: On the one hand, it is out of the question to take from a patient, who is often anaemic, multiple samples which would be necessary in order to monitor the efficiency of the treatment as it progresses. On the other hand, given the risks connected with the handling of possibly contaminated blood samples, the general tendency is to avoid such handling. Finally, the laboratory analysis of a blood sample is both costly and relatively long, which is incompatible with the desired objective.

The document EP 0 547 025 describes a method for the in vivo determination of the haemodialysis parameters which do not necessitate the carrying-out of measurements on blood. According to this method, whose implementation requires means for regulating the ionic concentration of the dialysis fluid and means for measuring the sodium concentration of the dialysis fluid or its conductivity, the electrolytic transfer of the dialysis fluid is measured at two different predetermined concentrations of the dialysis fluid and the dialysance is deduced therefrom.

This method necessitates exposing the patient to a dialysis fluid differing substantially from the dialysis fluid prescribed during the time necessary for the stabilization of the concentration of the dialysis fluid downstream of the exchanger, failing which the measurement applies to a dialysis fluid of intermediate concentration, and all the calculations subsequently made from this measurement are erroneous.

SUMMARY OF CERTAIN ASPECTS OF THE INVENTION

One aim of the invention is to design a method of the type mentioned above by means of which the representative parameters of the progress of the treatment can be frequently determined exactly and without, as a result, the patient having to be subjected for a long period to treatment conditions different from the prescribed conditions.

To achieve this aim, there is provided, according to the invention, a method for the determination of a significant parameter (Cb, D, K, Kt/V) of the progress of an extracorporeal treatment of blood carried out in an apparatus for treating blood provided with means for circulating the blood of a patient and a treatment fluid on both sides of the semipermeable membrane of a membrane exchanger, the method comprising steps of:

successively circulating in the exchanger at least a first (d1) and a second (d2) treatment fluid having a characteristic (Cd) linked to at least one of the significant parameters of the treatment (Cb, D, K, Kt/V), the value of the characteristic in the first fluid (d1) upstream of the exchanger being different from the value of the characteristic (Cd) in the second fluid (d2) upstream of the exchanger, measuring in each of the first (d1) and second (d2) treatment fluids two values (Cd1in, Cd1out; Cd2in, Cd2out) of the characteristic (Cd), respectively upstream and downstream of the exchanger, the method being characterized in that it comprises, in addition, the steps of:

putting into circulation a third (d3) treatment fluid in the exchanger while the characteristic (Cd) in the second fluid (d2) has not reached a stable value downstream of the exchanger, the value of the characteristic (Cd) in the third fluid (d3) upstream of the exchanger being different from the value of the characteristic (Cd) in the second fluid (d2) upstream of the exchanger, measuring two values (Cd3in, Cd3out) of the characteristic (Cd) in the third fluid (d3) respectively upstream and downstream of the exchanger, and calculating a value of a significant parameter of the progress of the treatment (Cb, D, K, Kt/V) from the measured values of the characteristic (Cd) in the first (d1), the second (d2) and the third (d3) treatment fluids.

At the calculation step, instead of the measured value (Cd1in, Cd2in, Cd3in) of the characteristic (Cd) in the first (d1), the second (d2) and the third (d3) treatment liquids, it is possible to use corresponding reference values ($Cd1in_{REF}$, $Cd2in_{REF}$, $Cd3in_{REF}$) which are entered before each treatment session in a control unit controlling the preparation of the treatment liquid.

This method has the advantage of permitting a precise determination of the significant parameters of the progress of the treatment from measurements carried out at short time intervals. In this manner, the patient is exposed for only a very short time to a treatment fluid different from the prescribed treatment fluid (for example too high or too low in sodium) and the method can be carried out as often as necessary for an appropriate monitoring of the treatment session.

According to one characteristic of the invention, the time interval (t2–ta) between the instant (ta), where the second fluid (d2) is put into circulation in the exchanger, and the instant (t2), where the value (Cd2out) of the characteristic (Cd) in the second fluid is measured downstream of the exchanger, is chosen such that the characteristic (Cd) has not reached a stable value at the instant (t2) downstream of the exchanger. In addition, the time interval (t3–tb) between the instant (tb), where the third fluid (d3) is put into circulation in the exchanger, and the instant (t3), where the value (Cd3out) of the characteristic (Cd) in the third fluid is measured downstream of the exchanger, is chosen such that the characteristic (Cd) has not reached a stable value at the instant (t3) downstream of the exchanger.

In one embodiment of the invention, the time intervals (t2–ta) and (t3–tb) are chosen substantially equal and the value of the characteristic (Cd) in the third fluid (d3) is chosen substantially equal to the value of the characteristic (Cd) in the first fluid (d1). The prescribed treatment fluid can be used as first fluid for the purposes of the invention.

According to another characteristic of the invention, the method comprises, in addition, the step of calculating at least a second, approximate value of the same significant treatment parameter (Cb, D, K, Kt/V). It is then possible to compare these values and to emit an error signal if they do not confirm a predefined law. This makes it possible to check that no undesirable event occurred which disturbed the conditions for the measurement. As example of disturbance, there may be mentioned the increase in the rate of blood recirculation in the treatment system, which may result from a movement of the patient, or alternatively the injection of a fluid into the extracorporal blood circuit connecting the patient to the exchanger.

Other characteristics and advantages of the invention will emerge on reading the following description. With reference to the drawings.

DETAILED DESCRIPTION OF THE PREFERRED EMBODIMENTS

Figure 1:
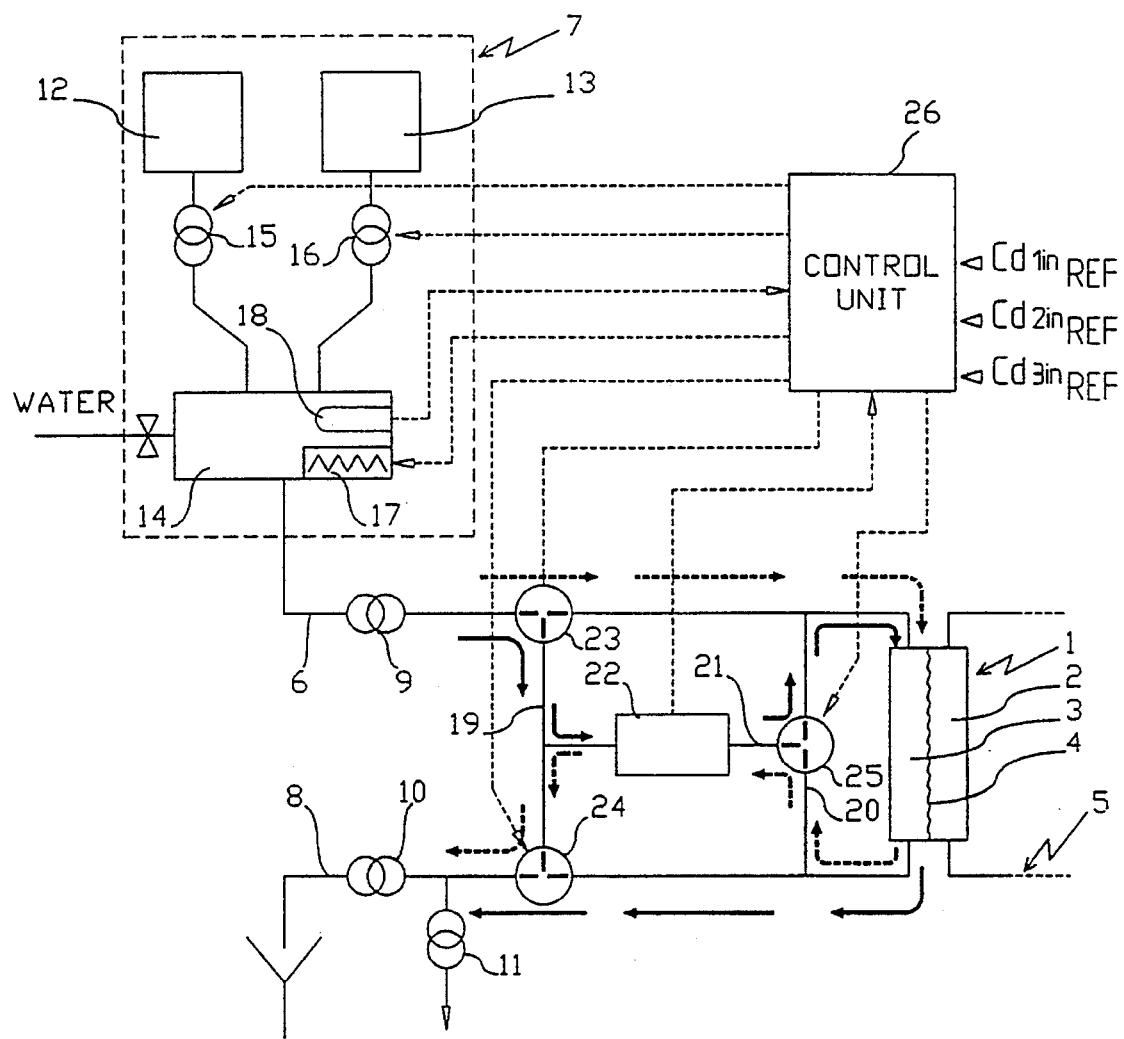
FIG. 1 is a partial schematic diagram of a haemodialysis/haemodiafiltration installation suitable for the implementation of the method according to the invention.

The haemodialysis/haemodiafiltration installation represented in FIG. 1 comprises an exchanger 1, such as a haemodialyser or a haemofilter, having a first and a second compartment 2, 3 which are separated by a semipermeable membrane 4.

The first compartment 2 is connected to a circuit 5 for extracorporeal circulation of blood and the second compartment 3 is connected to a circuit for dialysis fluid comprising a feed pipe 6 connecting a generator 7 of dialysis fluid to an inlet of the second compartment. A discharge pipe 8 connects an outlet of the second compartment 3 to a waste water circuit.

A first circulation pump 9 is placed on the feed pipe 6 and a second pump 10 is placed on the discharge pipe 8, the output of this second pump being regulated by non-represented means so as to be equal to the output of the first pump. An extraction pump 11 is connected to the discharge pipe 8, upstream of the second pump 10, in order to extract from the dialysis circuit, where appropriate, a metered quantity of used fluid corresponding to the quantity of plasma water which is removed from the patient by ultrafiltration.

The generator 7 of dialysis fluid comprises two reservoirs 12, 13 for concentrated solutions connected to a preparation reservoir 14 for the metered mixing of two concentrated solutions with water. The flow rate of the solutions in the preparation reservoir 14 can be regulated respectively by two pumps 15, 16. The concentrated solutions, which are of complementary compositions, comprise, in combination, the principal blood electrolytes (sodium, potassium, calcium, magnesium, chlorides and bicarbonates). A heating device 17 and a conductivity probe 18 are placed in the preparation reservoir 14.

The installation is also equipped with a circuit for measuring the characteristics of the dialysis fluid permitting a measurement to be carried out on the fresh dialysis fluid and a measurement on the used fluid by means of the same probe, for each characteristic considered. To this end, the measuring circuit comprises a first and a second secondary line 19, 20 branching off from the exchanger 1 between the feed line 6 and the discharge line 8 of the dialysis fluid circuit, as well as a joining line 21, connecting the first to the second secondary line, in which is placed a measuring cell 22 containing one or more probes for measuring the characteristics of the dialysis fluid. The first secondary line 19 is connected respectively to the feed 6 and discharge 8 lines by means of two three-way valves 23, 24 and the joining line 21 is connected to the second secondary line 20 by means of a three-way valve 25. Depending on the arrangement of the valves 23, 24, 25, it is the fresh dialysis fluid (solid arrows) or the used fluid (dotted arrows) which circulate in the measuring cell 22.

A calculation and control unit 26 controls the operation of the installation as a function of set values which are initially supplied to it for the treatment parameters, in particular, the blood flow rate, the dialysis fluid flow rate, the ultrafiltration rate, the temperature and the electrolytic concentration of the dialysis fluid, and the duration of the treatment session. Within the specific framework of the invention, the control unit 26 initiates at regular intervals, according to a predetermined sequence, the taking of a series of measurements on the dialysis fluid. In accordance with the method described later, this measurement phase requires the successive production of three dialysis fluids of different nominal conductivity by the dialysis generator 7, the switching of the valves 23, 24, 25 from one position into the other so that the measuring cell 22 is irrigated, for each of the three dialysis fluids, with fresh fluid and used fluid, and finally the precise sequencing of the actual taking of the measurement.

For the sake of clarity, known components and accessories of a haemodialysis/haemodiafiltration installation whose description would not facilitate the understanding of the invention, such as, especially, means for the measurement of pressure in the various circuits and means for the measurement of the flow rate Qd of the dialysis fluid and for the measurement of the ultrafiltration rate Quf, were not represented in FIG. 1.

As recalled above, a principle of the invention consists of measuring certain characteristics of the treatment fluid (dialysis fluid) so as to deduce from it, by calculation, the real value of the corresponding blood characteristics, as well as the real value of the significant parameters of the efficiency of the treatment, which are linked to these blood characteristics.

The measuring cell 22 may thus contain a temperature probe, a conductivity probe, an electrode for measuring the concentration of such solute, a pH probe and a probe for measuring the partial pressure of $CO_2$, and the like.

In the text which follows, the method according to the invention will be described by taking the example, which cannot be considered as being limitative, of a conductivity measurement. It is recalled that an excellent correlation exists between the conductivity of the dialysis fluid and its concentration of ionized substances, of which sodium represents the predominant part. It is by virtue of this correlation that it is possible to calculate the real concentration (Cbin) of blood sodium at the inlet of the exchanger from four measured values of the conductivity of the dialysis fluid (Cd1in, Cd2in, Cd1out, Cd2out, respectively the conductivity at the inlet and the outlet of the exchanger, measured during the successive passage of a first and of a second dialysis fluid d1, d2 having different conductivities), by application of the formula:

$$Cbin = \frac{Cd2out \times Cd1in - Cd1out \times Cd2in}{(Cd1in - Cd1out) - (Cd2in - Cd2out)} \quad (1)$$

which is deduced from the general formula for the dialysance D:

$$D = \frac{-(Qd + Quf) \times (Cdin - Cdout)}{Cbin - Cdin} \quad (2)$$

where Qd is the flow rate of the liquid in the compartment of the exchanger connected to the dialysis circuit, Quf is the ultrafiltration rate, Cdin and Cdout the conductivity/concentration of ionized substances of the dialysis fluid upstream and downstream of the exchanger and Cbin, the blood sodium concentration upstream of the exchanger.

Knowing the real value of the concentration Cbin of sodium in the blood at the inlet of the exchanger, the real dialysance D of the system can be calculated by means of the formula (2).

Knowing, in addition, that there are tables of correspondence between the dialysance for sodium and the clearance for urea, the real clearance K of the exchanger for urea can be deduced from the calculated real dialysance D.

Finally, from the real clearance K, the time t elapsed from the beginning of the treatment and the volume V of distribution of urea in the patient (which depends on the average weight, the sex and the age), the dose of dialysis administered Kt/V can be calculated.

In accordance with the invention, in order to avoid subjecting the patient to treatment conditions beyond what is normal (dialysis fluid having a conductivity greater than or less than the prescribed conductivity) for a significant time, three series of conductivity measurements are carried out at close intervals on three dialysis fluids d1, d2, d3 of different nominal conductivities, the measurements on the second and third dialysis fluids d2, d3 downstream of the exchanger being taken before this conductivity has stabilized. The manner in which the various significant parameters of the progress of the treatment can be calculated exactly from measurements taken during a transition state of the dialysis fluid as regards the conductivity will now be explained in relation to FIG. 2.

Figure 2:
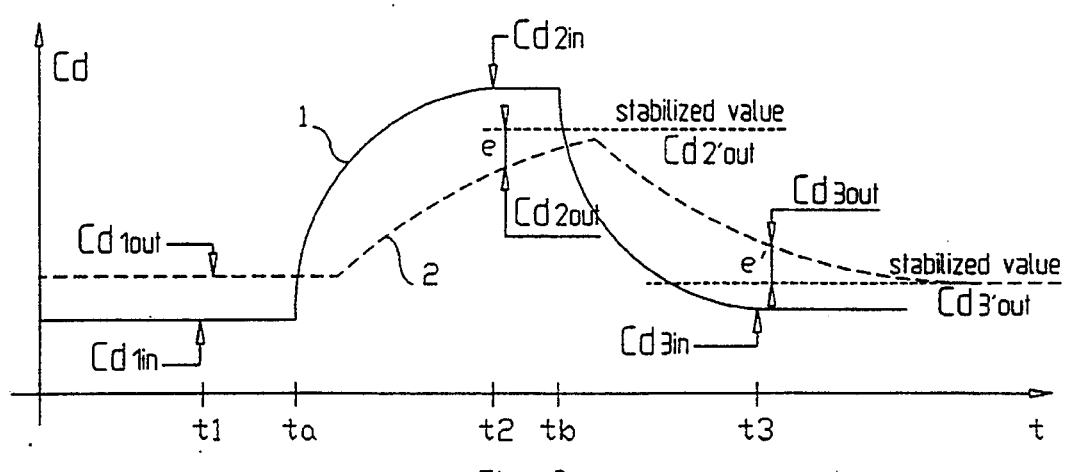
FIG. 2 is a graph representing the variation of the conductivity of the treatment fluid as a function of time during the implementation of the method according to the invention.

FIG. 2 represents two graphs of the conductivity of the dialysis fluid as a function of time, the graph 1, in the form of a solid line, corresponds to the variation of the conductivity upstream of the exchanger and the graph 2, in the form of a dotted line, corresponds to the variation of the conductivity downstream of the exchanger.

In accordance with these graphs, a first dialysis fluid d1 of constant conductivity, prepared by the generator 7, is put into circulation in the exchanger 1 until an instant ta. The conductivity of the dialysis liquid d1, is, as a general rule, substantially equal to the corresponding reference value $Cd1in_{REF}$ entered in the control unit 26 before the treatment session. This dialysis fluid is preferably that whose electrolytic composition was initially prescribed by the doctor. It can be noted that the conductivity downstream of the dialyser is greater than the conductivity upstream, which indicates that a transfer of ionized substances occurs in the exchanger, from the blood to the dialysis fluid. Prior to the instant ta, there are successively measured, by means of the measuring device represented in FIG. 1, the conductivity Cd1in of the first dialysis fluid upstream of the exchanger 1, then the conductivity Cd1 out downstream of the exchanger, this second measurement being taken at the instant t1. The measured values Cd1in and Cd1out are stored in a memory of the control and calculation unit 26. The generator 7 of dialysis fluid is then programmed to produce, for a short period of time tb–ta (for example two minutes), a second dialysis fluid d2 differing from the first dialysis fluid d1 by a higher, also constant, nominal conductivity. The conductivity of the dialysis liquid d2, is, as a general rule, substantially equal to the corresponding reference value $Cd2in_{REF}$ entered in the control unit 26 before the treatment session. What then circulates in the dialysis circuit is, for a period, a mixture of the first and second dialysis fluids d1, d2, where the proportion of the first decreases gradually, which the graphs translate by an ascending curve rapidly becoming flat and tending towards a horizontal asymptote. It can be noted that the conductivity upstream of the dialyser (graph 1) stabilizes rapidly, before the instant tb, whereas the conductivity downstream of the exchanger (graph 2) tends more slowly towards a constant value, which it did not reach at the instant tb. This is due to the fact that the conductivity downstream of the exchanger does not stop changing as long as the exchanger is not completely purged of the mixture resulting from the putting-into-circulation of the second dialysis fluid and as long as the diffusive transfer phenomena have not reached a state of equilibrium in the exchanger.

It can also be noted, in the ascending portion of the graphs, that the conductivity of the dialysis fluid at the inlet of the exchanger is greater than the conductivity of the dialysis fluid at the outlet of the exchanger, which indicates the fact that a diffusive transfer of ionized substances occurs, this time, from the dialysis fluid to the blood.

Prior to the instant tb, there are measured successively, by means of the measuring device represented in FIG. 1, the conductivity Cd2in of the second dialysis fluid upstream of the exchanger 1, and then the conductivity Cd2out downstream of the exchanger, this second measurement being taken at the instant t2. There is a difference e between the conductivity value Cd2out measured downstream of the exchanger 1 and what would be the exact or stabilized value Cd2'out of the conductivity of the second dialysis fluid d2 downstream of the exchanger if the second dialysis fluid d2 were put into circulation for a sufficiently long period in the dialysis fluid circuit, which, for the reasons mentioned above, is undesirable. The measured values Cd2in and Cd2out are stored in a memory of the control and calculation unit 26.

From the instant tb, the generator of dialysis fluid 7 is programmed to produce a third dialysis fluid d3 having a constant nominal conductivity less than the conductivity of the second dialysis fluid d2. The conductivity of the dialysis liquid d3, is, as a general rule, substantially equal to the corresponding reference value $Cd3in_{REF}$ entered in the control unit 26 before the treatment session. There then circulates for a period, in the dialysis circuit, a mixture of the second and third dialysis fluid d2, d3, where the proportion of the third dialysis fluid d3 increases rapidly, which the graphs indicate by a descending curve becoming flat and tending towards a horizontal asymptote corresponding to the conductivity value of the third dialysis fluid d3 respectively upstream (graph 1) and downstream (graph 2) of the exchanger. For the same reasons as during the circulation phase of the second dialysis fluid, the conductivity upstream of the exchanger stabilizes more quickly than the conductivity downstream of the exchanger, finally reaching the conductivity value of the third dialysis fluid d3. It can be noted that, shortly after the instant tb, a reversal of the direction of the diffusive transfer of the ionized substances in the exchanger occurs, these substances again migrating from the blood to the dialysis fluid.

When the conductivity upstream of the exchanger is stabilized and while the conductivity downstream of the exchanger is still decreasing, the value of these conductivities, Cd3in and Cd3out respectively, is measured successively, the measurement of the conductivity downstream of the exchanger being taken at the instant t3 and this value differing from the stabilized value Cd3'out (conductivity of the third dialysis fluid d3) by a quantity e'. The measured values Cd3in and Cd3out are stored in a memory of the control and calculation unit 26.

At the end of the measurement-taking stage which has just been described, the control and calculation unit therefore has in memory six measured values Cd1in, Cd1out, Cd2in, Cd2out, Cd3in, Cd3out, which are not directly exploitable by application of the formula 1, which is exact only for the stabilized conductivity values.

According to the invention, in order to calculate the concentration Cbin of blood sodium upstream of the exchanger or the real dialysance D of the system, the starting point is the observation that the quantities e, e' depend only on three factors: the amplitude of the disturbance (Cd2in–Cd1in, Cd3in–Cd2in) induced in the system by the putting-into-circulation of the second dialysis fluid d2 and the third dialysis fluid d3; the instant for the measurement (t2, t3) relative to the beginning of the disturbance (ta, tb); and the time constant θ for the system, which depends on the flow rates of the dialysis fluid and of the blood, on the surface area of the membrane 4 and the coefficient of diffusion of the membrane for the solute considered, here sodium.

Consequently, by choosing two disturbances whose amplitudes are equal in absolute value, as well as time intervals between the beginning of each disturbance and the corresponding measurement which are equal (t2–ta=t3–tb), it is ensured that the quantities e and e' are equal, so that, by applying the formula (2), the calculation of Cbin or of D will be done simply by resolution of three equations with three unknowns, Cbin, D and e, the flow rate of dialysis fluid and the rate of ultrafiltration Qd and Quf being moreover known. Other significant parameters of the progress of the dialysis session, such as the clearance K or the dose of dialysis Kt/V will be immediately deduced from the calculation of the real blood sodium concentration Cbin or of the real dialysance D.

As example, the above mentioned system of equations can be put in the following form:

$$Cbin = \frac{Cd1out - (1-A) \times Cdin}{A}$$

$$D = (Qd + Quf) \times A$$

where $$A = 1 - \frac{(2 \times Cd1out - Cd2out - Cd3out)}{2 \times Cd1in - Cd2in - Cd3in}$$

Moreover, according to the invention, several values of the same parameter are calculated so as to check if an accidental disturbance occurred during the above-described stage for taking measurements. For example, three values of the dialysance D can be calculated, a first exact value D0 as a function of six measurements of conductivity, a second approximate value D1 as a function of Cd1in, Cd1out, Cd2in, Cd2out and a third approximate value D2 as a function of Cd2in, Cd2out, Cd3in, Cd3out. Next, it is checked if the three values thus calculated obey one or more predefined laws such as: D0 less than or equal to D1 and D1 less than or equal to D2, or alternatively the difference D0–D1 is equal or substantially equal to the difference D1–D2. In the case where one of these laws may not be respected, an error signal is emitted.

The invention which has just been described can have variants, both as regards the actual stage for taking measurements (choice of the value of the nominal conductivity of the various dialysis fluids, that is to say also the amplitude and the direction of the disturbance induced in the system, and choice of the instant where the measurements are taken as a function of the beginning of the successive disturbances) and the manner in which the significant parameters of the course of the treatment are calculated from the measured conductivity values.

As regards the choice of the direction of the echelon of conductivity between two dialysis fluids put into circulation successively, all combinations are possible. As example:

The value of the characteristic Cd in the first fluid d1 is chosen less than the value of the characteristic Cd in the second fluid d2, which is itself chosen less than the value of the characteristic Cd in the third fluid d3.

The value of the characteristic Cd in the first fluid d1 is chosen greater than the value of the characteristic Cd in the second fluid d2, which is itself chosen greater than the value of the characteristic Cd in the third fluid d3.

The value of the characteristic Cd in the first fluid d1 is chosen less than the value of the characteristic Cd in the second fluid d2, which is itself chosen greater than the value of the characteristic Cd in the third fluid d3.

The value of the characteristic Cd in the first fluid d1 is chosen greater than the value of the characteristic Cd in the second fluid d2, which is itself chosen less than the value of the characteristic Cd in the third fluid d3.

The value of the characteristic Cd in the second fluid d2 upstream of the exchanger is chosen less than or greater than the value of the characteristic Cd in the first fluid d1 upstream of the exchanger, according to the sign of the difference (Cdin1–Cdout1) between the measured values of the characteristic Cd in the first fluid d1 upstream and downstream of the exchanger.

The value of the characteristic Cd in the third fluid d3 upstream of the exchanger is chosen less than or greater than the value of the characteristic Cd in the second fluid d2 upstream of the exchanger, according to the sign of the difference (Cdin1–Cdout1) between the measured values of the characteristic Cd in the first fluid d1 upstream and downstream of the exchanger and/or according to the sign of the difference (Cdin2–Cdout2) between the measured values of the characteristic Cd in the second fluid d2 upstream and downstream of the exchanger.

The value of the characteristic Cd in the third fluid d3 upstream of the exchanger is chosen as a function of an approximate value of the blood sodium concentration Cb', calculated as a function of the measured values Cd1in, Cd1out, Cd2in, Cd2out on the first and second dialysis fluids d1, d2: for example, the value of the characteristic Cd is chosen equal to or very different from Cb'.

In all the abovementioned examples, the first dialysis fluid can be the dialysis fluid prescribed for the treatment. With the exception of the first two examples, the third dialysis fluid can be chosen substantially identical to the dialysis fluid prescribed for the treatment.

As regards the amplitude of the echelons of conductivity (Cd2in–Cd1in, Cd3in–Cd2in) and the duration of the time intervals between the beginning of each disturbance and the instant for the corresponding measurement (t2–ta, t3–tb), all the combinations are still possible, provided that these echelons and these intervals are sufficiently high for the measured values to be significant.

As example, the two echelons of conductivity and/or the two measurement intervals can be chosen so that, although respectively of different amplitudes and/or durations, the quantities e and e' are substantially equal, in which case the method of calculation set out above is applicable.

If it happened on the contrary that, as a result of these choices, the quantities e and e' are not equal, a method of calculation could consist in measuring the stabilized value Cd3'out for the third dialysis fluid d3 downstream of the exchanger, in calculating e'= Cd3out–Cd3'out, then in calculating e as a function of e', from which the stabilized value for the second dialysis fluid d2 downstream of the exchanger, which is inaccessible to the measurement, could be calculated. Three pairs of measured/calculated values of the conductivity of the three dialysis fluids would then be available which can be used in pairs in the equation (1). Another method of calculation consists in resolving the following system of equations:

$$Cbin = \frac{Cd1out - (1-A) \times Cd1in}{A}$$

$$D = (Qd + Quf) \times A$$

where $$A = 1 - \frac{(2 \times Cd1out - Cd2'out - Cd3'out)}{(2 \times Cd1in - Cd2in - Cd3in)}$$

$$Cd1out = (1-A)\, Cd1in + ACbin$$

$$\begin{aligned}
Cd2'out &= Cd2out + e \\
&= Cd1out + \\
&\quad (1-A)(Cd2in - Cd1in)(1 - \exp(ta - t2)/\theta) \\
Cd3'out &= Cd3out - e' \\
&= Cd1out + \\
&\quad (1-A)(Cd2in - Cd1in)(1 - \exp(ta - t3)/\theta) + \\
&\quad (1-A)(Cd3in - Cd2in)(1 - \exp(tb - t3)/\theta)
\end{aligned}$$

θ being the time constant for the system, which, as mentioned above, depends on the flow rates of the dialysis fluid and the blood, on the surface area of the membrane 4 and on the coefficient of diffusion of the membrane for the solute considered. The present invention is not limited to the embodiments which have just been described and it is capable of variants. For example, in the calculation steps of the method, where the value of the conductivity of the treatment liquids d1, d2, d3, upstream of the exchanger 1 are taken into consideration, it is possible, instead of measured values Cd1in, Cd2in, Cd3in, to use corresponding reference values $Cd1in_{REF}$, $Cd2in_{REF}$, $Cd3in_{REF}$, which are entered before each treatment session in a control unit controlling the preparation of the treatment liquid.

It can also be understood that the method according to the invention can be used on installations other than the installation described above. The generator of dialysis fluid could be an on-line generator. Likewise, instead of using the same probe to take measurements both on the fresh dialysis fluid and on the used fluid, a probe could be placed upstream of the exchanger and a probe downstream.

We claim:

1. A method for determining a significant parameter (Cb, D, K, Kt/V) of the progress of an extracorporeal blood treatment carried-out using an apparatus for treating blood, the apparatus being provided with means for circulating blood of a patient and a treatment fluid on opposing sides of a semipermeable membrane in a membrane exchanger, the method comprising the steps of:

circulating through the exchanger a first treatment fluid (d1), having a characteristic (Cd) linked to at least one of the significant treatment parameters (Cb, D, K, Kt/V);

measuring two, values (Cd1in, Cd1out) of the characteristic (Cd) in the first treatment fluid (d1), respectively upstream and downstream of the exchanger;

circulating through the exchanger a second treatment fluid (d2), having the characteristic (Cd) with a value (Cd2in) upstream of the exchanger different from the value of (Cd1in);

measuring two values (Cd2in, Cd2out) of the characteristic (Cd) in the second treatment fluid (d2), respectively upstream and downstream of the exchanger;

circulating through the exchanger, before the characteristic (Cd) of the second fluid (d2) has reached a stable value downstream of the exchanger, a third treatment fluid (d3) having the characteristic (Cd), a value (Cd3in) of the characteristic (Cd) in the third fluid (d3) upstream of the exchanger being different from the value of (Cd2in);

measuring two values (Cd3in, Cd3out) of the characteristic (Cd) in the third fluid (d3) respectively upstream and downstream of the exchanger; and calculating, using the measured values of (Cd1in), (Cd1out), (Cd2in), (Cd2out), (Cd3in), and (Cd3out), at least one value of at least one significant parameter of the progress of the treatment (Cb, D, K, Kt/V).

2. A method according to claim 1, wherein, upstream of the exchanger, the value of the characteristic (Cd) in the first fluid (d1) is chosen less than the value of the characteristic (Cd) in the second fluid (d2), which is itself chosen less than the value of the characteristic (Cd) in the third fluid (d3).

3. A method according to claim 1, wherein, upstream of the exchanger, the value of the characteristic (Cd) in the first fluid (d1) is chosen greater than the value of the characteristic (Cd) in the second fluid (d2), which is itself chosen greater than the value of the characteristic (Cd) in the third fluid (d3).

4. A method according to claim 1, wherein, upstream of the exchanger, the value of the characteristic (Cd) in the first fluid (d1) is chosen less than the value of the characteristic (Cd) in the second fluid (d2), which is itself chosen greater than the value of the characteristic (Cd) in the third fluid (d3).

5. A method according to claim 1, wherein, upstream of the exchanger, the value of the characteristic (Cd) in the first fluid (d1) is chosen greater than the value of the characteristic (Cd) in the second fluid (d2), which is itself chosen less than the value of the characteristic (Cd) in the third fluid (d3).

6. A method according to claim 1, wherein the value of the characteristic (Cd) in the second fluid (d2) upstream of the exchanger is chosen less than or greater than the value of the characteristic (Cd) in the first fluid (d1) upstream of the exchanger, according to the sign of the difference (Cdin1–Cdout1) between the measured values of the characteristic (Cd) in the first fluid (d1) upstream and downstream of the exchanger.

7. A method according to claim 1, wherein the value of (Cd3in) differs from the value of (Cd2in), according to a sign of a difference (Cd1in–Cd1out) between the measured values of the characteristic (Cd) in the first fluid (d1) upstream and downstream of the exchanger and/or according to a sign of a difference (Cdin2–Cdout2) between the measured values of the characteristic (Cd) in the second fluid (d2) upstream and downstream of the exchanger.

8. A method according to claim 1, wherein the value of (Cd3in) is chosen as a function of an approximate value of blood sodium concentration (Cb'), calculated as a function of the measured values (Cd1in, Cd1out, Cd2in, Cd2out) of the first and second dialysis fluids (d1, d2).

9. A method according to claim 1, wherein the measured characteristic (Cd) is chosen from the group consisting of sodium concentration and conductivity, and a parameter of the treatment which is calculated is the concentration of sodium (Cb) in the blood upstream of the exchanger.

10. A method according to claim 9, wherein the concentration of sodium (Cb) in the blood upstream of the exchanger is calculated according to the formula:

$$Cb = \frac{Cd1out - (1-A) \times Cd1in}{A}$$

where $$A = 1 - \frac{(2 \times Cd1out - Cd2out - Cd3out)}{(2 \times Cd1in - Cd2in - Cd3in)}.$$

11. A method according to claim 1, wherein the measured characteristic (Cd) is chosen from the group consisting of sodium concentration and conductivity and wherein a parameter of the treatment which is calculated is the dialysance (D).

12. A method according to claim 11, wherein the dialysance (D) is calculated according to the formula:

$$D = (Qd + Quf) \times A$$

where

Qd is a flow rate of the dialysis fluid,
Quf is a rate of ultrafiltration, and $$A = 1 - \frac{(2 \times Cd1out - Cd2out - Cd3out)}{(2 \times Cd1in - Cd2in - Cd3in)}$$

13. A method according to claim 11, wherein a clearance (K) for a blood metabolite is deduced from the dialysance (D) using a predetermined correspondence table.

14. A method according to claim 13, wherein a parameter of the treatment which is calculated is a dose of dialysis (Kt/V), where t is a treatment time elapsed and V is a total volume of water for the patient.

15. A method according to claim 1, wherein, at the step of calculating at least a value of at least one significant parameter of the progress of the treatment (Cb, D, K, Kt/V), for the measured values Cd1in, Cd2in, Cd3in of the characteristic (Cd) in the first (d1), the second (d2) and the third (d3) treatment fluids, there are used corresponding reference values ($Cd1in_{REF}$, $Cd2in_{REF}$, $Cd3in_{REF}$), which are entered before each treatment session in a control unit controlling the preparation of the treatment fluids.

16. A method for determining a significant parameter (Cb, D, K, Kt/V) of the progress of an extracorporeal blood treatment carried-out using an apparatus for treating blood, the apparatus being provided with means for circulating blood of a patient and a treatment fluid on opposing sides of a semipermeable membrane in a membrane exchanger, the method comprising the steps of:

circulating through the exchanger a first treatment fluid (d1), having a characteristic (Cd) linked to at least one of the significant treatment parameters (Cb, D, K, Kt/V);

measuring two values (Cd1in, Cd1out) of the characteristic (Cd) in the first treatment fluid (d1), respectively upstream and downstream of the exchanger;

circulating through the exchanger a second treatment fluid (d2), having the characteristic (Cd) with a value (Cd2in) upstream of the exchanger different from the value of (Cd1in);

measuring two values (Cd2in, Cd2out) of the characteristic (Cd) in the second treatment fluid (d2), respectively upstream and downstream of the exchanger, whereby a time interval (t2–ta) between an instant (ta), when the second fluid (d2) is put into circulation in the exchanger, and an instant (t2), when the value (Cd2out) of the characteristic (Cd) in the second fluid is measured downstream of the exchanger, is chosen such that the characteristic (Cd) has not reached a stable value downstream of the exchanger at the instant (t2);

circulating through the exchanger before the characteristic (Cd) of the second fluid (d2) has reached a stable value downstream of the exchanger, a third treatment fluid (d3) having the characteristic (Cd), a value (Cd3in) of the characteristic (Cd) in the third fluid (d3) upstream of the exchanger being different from the value of (Cd2in);

measuring two values (Cd3in, Cd3out) of the characteristic (Cd) in the third fluid (d3) respectively upstream and downstream of the exchanger, whereby a time interval (t3–tb) between an instant (tb), when the third fluid (d3) is put into circulation in the exchanger, and an instant (t3), when the value (Cd3out) in the third fluid is measured downstream of the exchanger, is chosen such that the characteristic (Cd) has not reached a stable value downstream of the exchanger at the instant (t3); and calculating, using the measured values of (Cd1in), (Cd1out), (Cd2in), (Cd2out), (Cd3in), and (Cd3out), at least one value of at least one significant parameter of the progress of the treatment (Cb, D, K, Kt/V).

17. A method for determining a significant parameter (Cb, D, K, Kt/V) of the progress of an extracorporeal blood treatment carried-out in an apparatus for treating blood, the apparatus being provided with means for circulating blood of a patient and a treatment fluid on opposing sides of a semipermeable membrane in a membrane exchanger, the method comprising the steps of:

circulating through the exchanger a first treatment fluid (d1) having a characteristic (Cd) linked to at least one of the significant parameters of the treatment (Cb, D, K, Kt/V);

measuring two values (Cd1in, Cd1out) of the characteristic (Cd) in the first treatment fluid (d1), respectively upstream and downstream of the exchanger;

circulating through the exchanger a second treatment fluid (d2), having the characteristic (Cd) with a value (Cd2in) upstream of the exchanger different from the value (Cd1in);

measuring two values (Cd2in, Cd2out) of the characteristic (Cd) in the second treatment fluid (d2), respectively upstream and downstream of the exchanger, whereby a time interval (t2–ta) between an instant (ta) when the second fluid (d2) is put into circulation in the exchanger, and an instant (t2) when the value (Cd2out) of the characteristic (Cd) in the second fluid is measured downstream of the exchanger, is chosen such that the characteristic (Cd) has not reached a stable value downstream of the exchanger at the instant (t2);

circulating through the exchanger before the characteristic (Cd) of the second fluid (d2) has reached a stable value downstream of the exchanger, a third treatment fluid (d3) having the characteristic (Cd), the value of the characteristic (Cd) in the third fluid (d3) upstream of the exchanger (Cd3in) being substantially equal to the value of (Cd2in);

measuring two values (Cd3in, Cd3out) of the characteristic (Cd) in the third fluid (d3) respectively upstream and downstream of the exchanger, whereby a time interval (t3–tb) between an instant (tb) when the third fluid (d3) is put into circulation in the exchanger, and an instant (t3), when the value (Cd3out) of the characteristic (Cd) in the third fluid is measured downstream of the exchanger, is chosen such that the characteristic (Cd) has not reached a stable value downstream of the exchanger at the instant (t3), and wherein the time intervals (t2–ta) and (t3–tb) are chosen to be substantially equal; and calculating, using the measured values of (Cd1in), (Cd1out), (Cd2in), (Cd2out), (Cd3in), and (Cd3out), at least one value of at least one significant parameter of the progress of the treatment (Cb, D, K, Kt/V).

18. A method for determining a significant parameter (Cb, D, K, Kt/V) of the progress of an extracorporeal treatment of blood carried-out in an apparatus for treating blood, the apparatus being provided with means for circulating blood of a patient and a treatment fluid on opposing sides of the semipermeable membrane of a membrane exchanger, the method comprising the steps of:

circulating through the exchanger a first treatment fluid (d1) having a characteristic (Cd) linked to at least one of the significant treatment parameters (Cb, D, K, Kt/V);

measuring two values (Cd1in, Cd1out) of the characteristic (Cd) in the first treatment fluid (d1), respectively upstream and downstream of the exchanger;

circulating through the exchanger a second treatment fluid (d2) having the characteristic (Cd) with a value (Cd2in) upstream of the exchanger different from the value of (Cd1in);

measuring two values (Cd2in, Cd2out) of the characteristic (Cd) in the second treatment fluid (d2), respectively upstream and downstream of the exchanger;

circulating through the exchanger before the characteristic (Cd) of the second fluid (d2) has reached a stable value downstream of the exchanger, a third treatment fluid (d3) having the characteristic (Cd), a value (Cd3in) of the characteristic (Cd) in the third fluid (d3) upstream of the exchanger being different from the value of (Cd2in);

measuring two values (Cd3in, Cd3out) of the characteristic (Cd) in the third fluid (d3), respectively upstream and downstream of the exchanger;

calculating, using the measured values of (Cd1in), (Cd1out), (Cd2in), (Cd2out), (Cd3in), and (Cd3out), at least a first and a second value of a same significant parameter of the progress of the treatment (Cb, D, K, Kt/V);

comparing at least the first and the second calculated values; and emitting an error signal if the calculated values do not confirm a predefined law.

* * * * *

UNITED STATES PATENT AND TRADEMARK OFFICE
CERTIFICATE OF CORRECTION

PATENT NO. : 5,567,320
DATED : October 22, 1996
INVENTOR(S) : Nicolas GOUX et al.

It is certified that error appears in the above-indentified patent and that said Letters Patent is hereby corrected as shown below:

On the title page, item [54] and Col. 1,
  line 3, change "PROGESS" to --PROGRESS--.

Claim 1, col. 10, line 32, change "two, values" to --two values--.

Signed and Sealed this

Fourth Day of March, 1997

Attest:

BRUCE LEHMAN

*Attesting Officer*            *Commissioner of Patents and Trademarks*